United States Patent [19]

Sirkin et al.

[11] Patent Number: 4,806,186

[45] Date of Patent: Feb. 21, 1989

[54] METHOD FOR PRODUCING A MASS PRODUCTION EAR PLUG

[75] Inventors: Robert Sirkin, Fullerton; Norman D. Best, Duarte, both of Calif.

[73] Assignee: Moldex Metric, Inc., Culver City, Calif.

[21] Appl. No.: 9,695

[22] Filed: Feb. 2, 1987

Related U.S. Application Data

[63] Continuation-in-part of Ser. No. 921,365, Oct. 20, 1986, abandoned.

[51] Int. Cl.⁴ .............................................. B32B 31/18
[52] U.S. Cl. .................................. 156/80; 156/257; 156/293; 128/864
[58] Field of Search ................. 156/80, 72, 257, 293; 128/151, 152; 181/129, 135; 381/183, 187; 2/423

[56] References Cited

U.S. PATENT DOCUMENTS

| 4,219,018 | 8/1980 | Draper | 128/152 |
| 4,253,452 | 3/1981 | Powers et al. | 156/293 |
| 4,293,355 | 10/1981 | Wacker | 128/152 |
| 4,314,553 | 2/1982 | Westerdal | 128/152 |

*Primary Examiner*—Caleb Weston
*Attorney, Agent, or Firm*—Thomas I. Rozsa; Charles H. Schwartz

[57] ABSTRACT

The present invention relates to a novel apparatus and method of manufacturing an ear plug assembly wherein the plug member is made of foam or similar material. By creating an assembly where the plug member can be confined in a chamber while gas is blown into the chamber, the plug member becomes semi-rigid and permits a piercing object to cut a slit in the plug member without causing it to buckle. If the speed of the cutting blade is at least 75 inches per second, the speed will compensate for the non-rigidity of the plug and it is not necessary to blow gas into the plug. Adhesive added at the location of the slit acts as a lubricant to permit a cord to be inserted into the plug member while at the same time acting as a bonding agent.

22 Claims, 5 Drawing Sheets

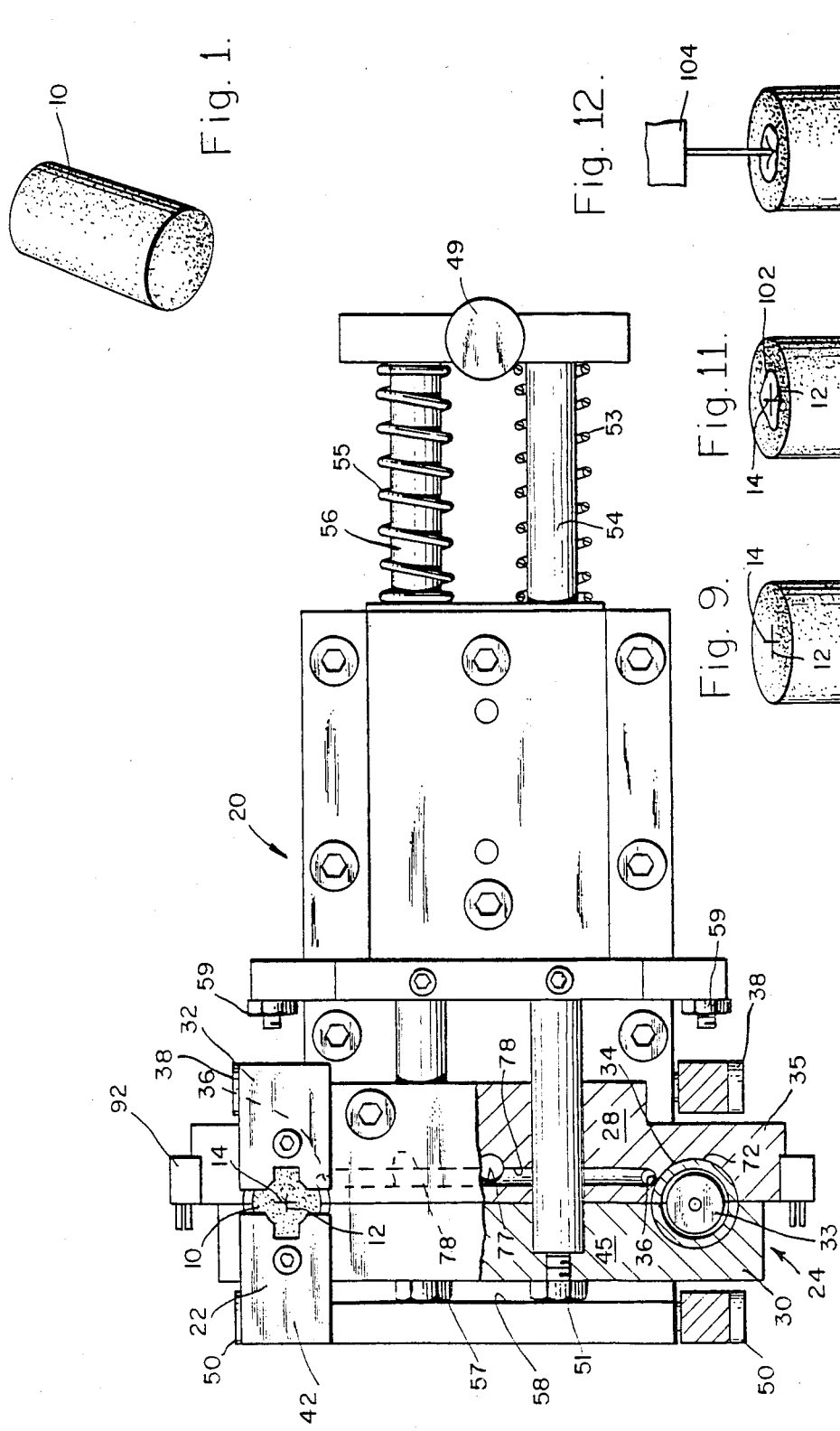

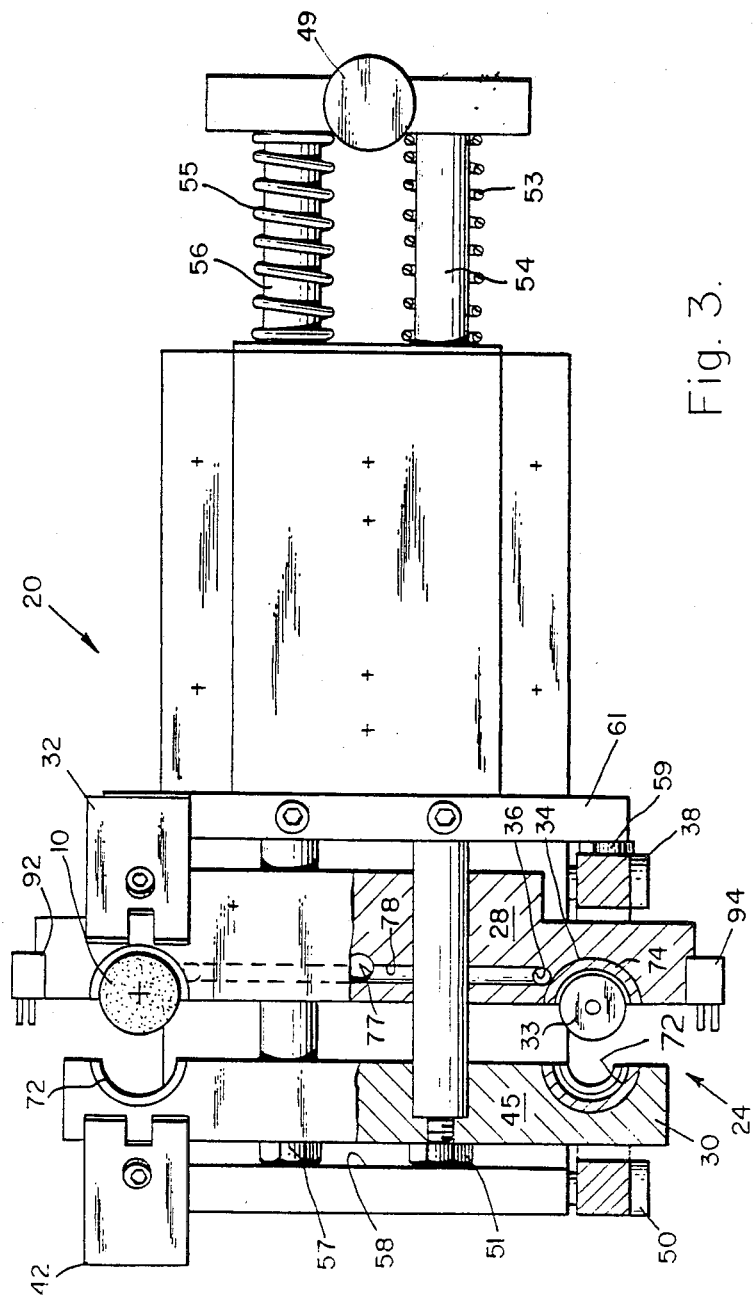

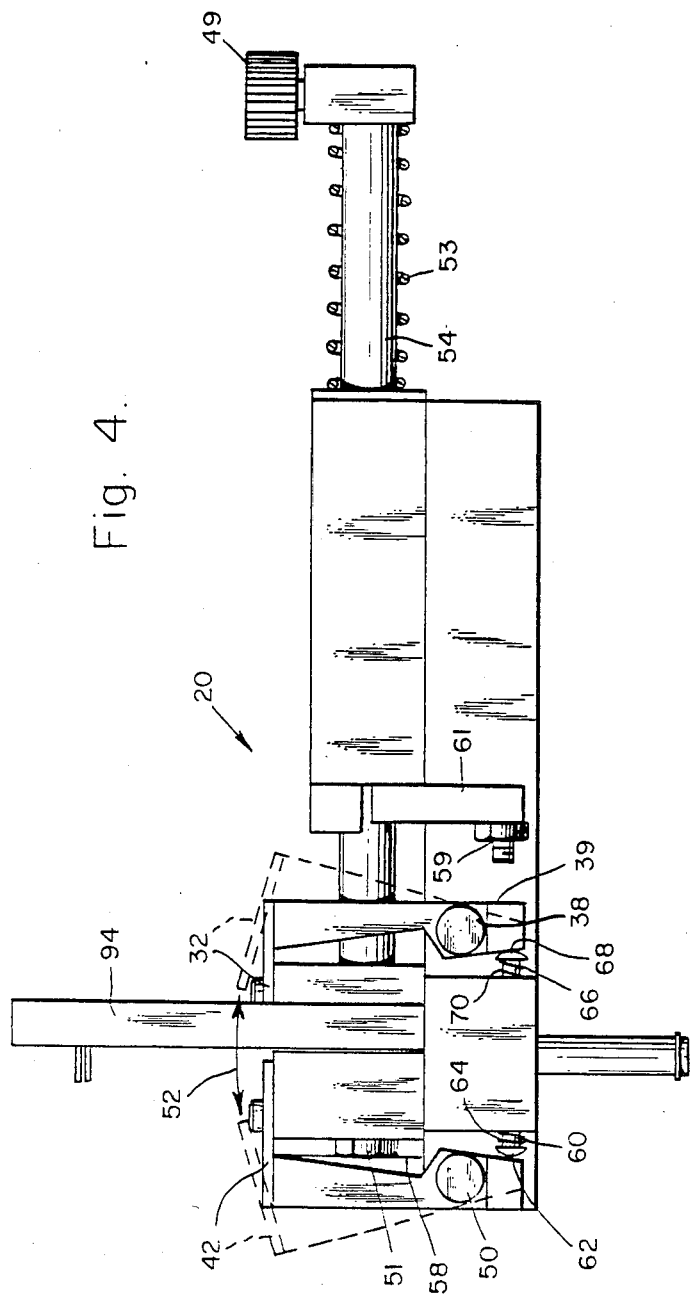
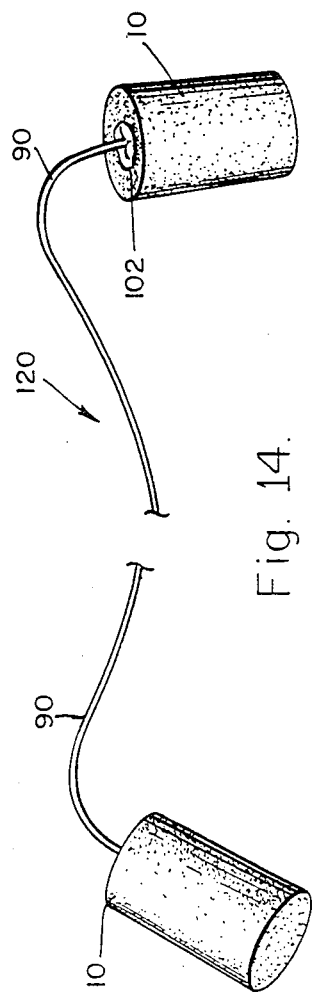

METHOD FOR PRODUCING A MASS PRODUCTION EAR PLUG

This is a continuation-in-part of copending application Ser. No. 921,365 filed on Oct. 20, 1986, abandoned.

BACKGROUND OF THE INVENTION

1. Field of the Invention

The present invention relates to an ear plug assembly which can be produced on a rapid mass production basis. Ear plug assemblies are comprised of a pair of plug members which are placed into the ear canal of both of a worker's ears to protect them from an extremely noisy environment in which he works. Since such ear plug members are lightweight and small, they can be easily lost. As a result, one improvement has been to tie the plug members together by means of a cord which is of sufficient length to permit a respective plug to be inserted into a respective ear canal. In this way, the plugs are securely placed into the ears to protect them and the joining cord reduces the likelihood that an ear plug will be lost if the assembly is set down or if one plug should accidentally fall out of the wearer's ear.

2. Background of the Invention

In general, ear plug assemblies have been in existence for many years. The concept of fastening the two ear plugs together in order to avoid losing them has also been in existence for many years. In general, ear plug assemblies were commonly made of a rubber like material since this permitted the ear plugs to be easily inserted into the wearer's ear canal. In recent years, polyvinyl and polyurethane foams and similar materials have been used for the ear plug. The use of polyvinyl chloride or polyurethane foam provides a flexible material which can be appropriately compressed in order to fit into the ear canal and which then subsequently expands in order to completely fill the ear canal space to thereby assure the maximum muffling of the external noise.

Since ear plug assemblies of this type are relatively inexpensive items which are frequently used and purchased in large quantities, the cost of manufacture is an important element in the ability to profitably sell such an item. Therefore, attempts have been made to improve the manufacturing process by which such ear plug assemblies have been made. One illustration of a prior art method of manufacture is disclosed in U.S. Pat. No. 4,253,452 issued to Powers et al. on Mar. 3, 1981 for Ear Plug Assembly. The concept of the Powers patent is to employ the characteristic that the ear plug members exhibit a slow recovery to normal structure when a sharp object is thrust into them. In the Powers patent, a sharp object is thrust into the foam plug member and permitted to remain inside the foam plug member for several seconds in order to create a hole inside the foam. Thereafter, the sharp object is removed and a flexible cord is inserted into the hole. The cord is permitted to remain in this position for several seconds while the foam returns to its original structure, thereby closing around the hole. A bonding agent can also be placed on the end of the cord before it is inserted into the open hole. The method of manufacture of the Powers patent contains several significant disadvantages. First, since the foam plug member is a very flexible and non-rigid structure, it is very difficult to imagine how the process described in Powers can actually work. As a sharp object is thrust into the foam member, the entire foam member itself would distort during the process and would be compressed. Therefore, a hole may be difficult to achieve or alternatively the hole would be pressed through the entire foam structure. A second major problem concerning the method described in Powers is the impractical manufacturing process. There is a waiting time of several seconds while the sharp object is thrust into the foam and an additional waiting time of several more seconds while the foam allegedly closes around the cord which has been placed inside the hole after the sharp object has been removed. Since the foam itself is not maintained in any sort of rigid fashion, the nature of the hole varies substantially from no hole at all to a hole through the entire plug member. It is therefore not possible to predict whether the cord can always be inserted into the hole (assuming it exists) and further how much time it would take for the hole to close, since the size of the hole may not always be consistent. In addition, the total waiting time is unacceptable for mass production processes. Therefore, the process disclosed in the Powers patent does not permit for a consistent and efficient manufacturing method to rapidly produce an ear plug assembly.

Applicant is unaware of any mass production method of manufacturing an ear plug assembly which temporarily causes the foam plug member to become rigid to thereby assure a consistently created opening in the plug member and further to assure that the extent of the opening is sufficient to permit an object such as a cord to be inserted therein. There is also no presently known process by which the cord can be inserted and immediately secured within the foam ear plug member without requiring any waiting time for the foam to close around the cord once it has been placed inside the opening created within the foam ear plug member.

SUMMARY OF THE INVENTION

The present invention relates to a novel apparatus and method of manufacturing an ear plug assembly wherein the plug member is made of foam like material.

It has been discovered, according to the present invention, that if the foam plug member which may be generally cylindrical in configuration and is made at least partially of open cell material is placed inside a housing member which may also be generally cylindrical in configuration and slightly larger than the foam plug member, and the housing member contains a plurality of spaced openings around its circumference, and then gas under pressure is blown into the housing member through the plurality of spaced openings, then the pressurized air will at least partially enter the foam member to thereby fill the cells of the foam member with air and cause it to be temporarily semi-rigid. With certain types of foam material, the semi-rigid condition may also be caused by chilling the foam material. By creating this semi-rigid condition in the foam, a sharp object can be thrust into the foam to consistently create a clean sharp opening therethrough. The semi-rigid condition of the foam will assure that the foam will not compress or distort under the impact of the sharp object's thrust.

It has also been discovered, according to the present invention, that if the speed of the sharp object is sufficiently high such as at least 75 inches per second for certain types of foam material when penetrating the surface of the foam, it is not necessary to fill the foam with gas prior to the cutting operation since the speed of insertion compensates for the non-rigidity of the foam. In this type of system, the foam material need not at least partially be made of open cell material.

It has further been discovered, according to the present invention, that if a slender knife is thrust into the semi-rigid foam in one direction and after the first knife is removed a second slender knife is subsequently thrust into the semi-rigid foam at approximately 90 degrees to the first thrust, then a pair of hairline slits set at approximately 90 degrees to each other is created in the foam to assure a sharp clean opening therethrough which will not cause a cavity or crater within the foam which must be resealed such as by allowing the foam to return to its normal position and fill in the crater. This substantially reduces manufacturing time.

It has additionally been discovered, according to the present invention, that if a small amount of liquid adhesive is placed on a flexible cord or at the hairline slit before the cord is placed into the hairline slit, the crossed hairline slit permits the lubricated flexible cord to be thrust into the foam member as though the flexible cord were in fact a rigid piece of material.

It has also been discovered that the embodiment of the present invention as described above can be used with mass production machinery to thereby mass produce a pair of foam member ear plugs connected by a flexible interconnecting member such as a piece of cord.

It has additionally been discovered, according to the present invention, that if an assembly is arranged wherein a predetermined amount of cord is cut before each end is placed into a respective one of the plug members, a completed ear plug assembly with a pair of plug members and the desired length of cord therebetween can be assembly in one convenient operation.

It is therefore an object of the present invention to provide an apparatus and method for rapidly mass producing an ear plug assembly comprised of a pair of foam or sponge like plug members which are connected by a flexible interconnecting member such as a cord.

It is another object of the present invention to provide an apparatus and method for permitting the soft flexible foam or sponge like ear plug member to be temporarily rigid during the time that slits are made in the foam and the flexible member is inserted therein to thereby assure that the opening created within the plug member is sharp and clean and to further assure that the flexible member will be inserted into the foam member on a rapid and consistent basis.

It is a further object of the present invention to provide an apparatus and method by which the temporary rigidity of the foam plug member and the creation of the opening therein and insertion of the cord within the plug member can be adopted to a mass production operation.

It is another object of the present invention to provide an apparatus and method whereby a predetermined length of interconnecting member such as cord is cut with a respective end inserted into one plug member each to thereby automatically create a completed ear plug assembly comprised of a pair of plug members interconnected by a desired length of cord.

Further novel features and other objects of the present invention will become apparent from the following detailed description, discussion and the appended claims, taken in conjunction with the drawings.

DRAWING SUMMARY

Referring particularly to the drawings for the purpose of illustration only and not limitation, there is illustrated:

FIG. 1 is a perspective view of a plug member which is one of the two flexible plug members of the ear plug assembly manufactured by the apparatus and method of the present invention.

FIG. 2 is a top plan view in partial cross-section of the nest assembly and its associated components.

FIG. 3 is a top plan view in partial cross-section of the nest assembly in the opened position.

FIG. 4 is a side elevational view of the nest assembly showing the plug retaining covers in dashed lines in the opened position.

FIG. 9 is a perspective view of the flexible plug member with a pair of slits created therein.

FIG. 11 is a perspective view of the plug member with a bonding agent applied at the location of the pair of slits.

FIG. 12 is a perspective view of the plug member with one end of a flexible interconnecting member being inserted into the plug member at the location of the slits.

Figure 13:
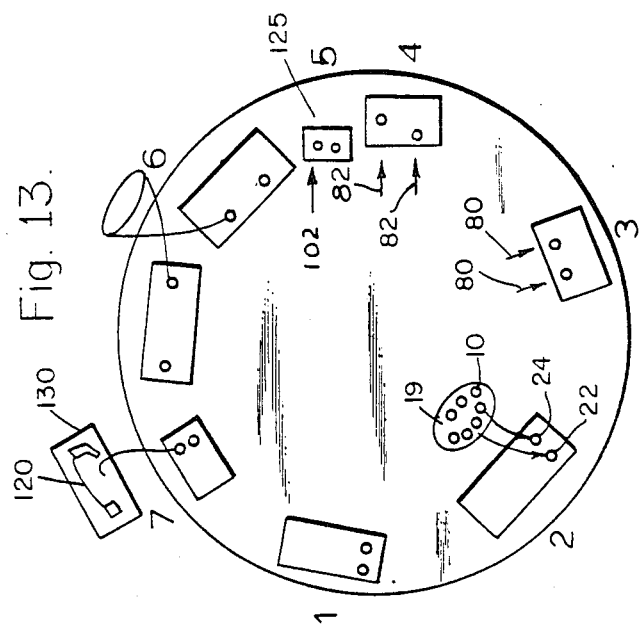

FIG. 13 a diagramatic view of a rotary dial showing the nest assembly moving from station to station in performing the tasks for producing the ear plug assemblies.

FIG. 14 is a perspective view of the final ear plug assembly comprising two flexible plug members interconnected by the flexible interconnecting member (shown broken at the middle for purposes of illustrating its substantial length relative to the two plug members.

DETAILED DESCRIPTION OF THE PREFERRED EMBODIMENT

Although specific embodiments of the invention will now be described with reference to the drawings, it should be understood that such embodiments are by way of example only and merely illustrative of but a small number of the many specific embodiments which can represent applications of the principles of the invention. Various changes and modifications obvious to one skilled in the art to which the invention pertains are deemed to be within the spirit, scope and contemplation of the invention as further defined in the appended claims.

The ear plug assembly of the present invention is created from a pair of flexible plug members interconnected by a flexible interconnecting means. Each plug member is made of resilient flexible foam or sponge-like material such as polyvinyl chloride or polyurethane. This material is at least partially open celled. A flexible plug member is shown at 10 in FIG. 1. While the plug member is shown as being generally cylindrical in shape, other shapes such as frustro-conical can also be used with the present invention. The apparatus for producing the ear plug assembly is shown in FIGS. 2 through 13. The present invention includes the formation of two duplicate plug members being formed with a desired length of interconnecting means having each of its ends simultaneously inserted into a respective plug member in order to arrive at the final ear plug assembly. It will also be appreciated that the apparatus to be described can be places on a mass production machine such as on a rotary dial machine where the method is run through a series of operation steps on the rotary dial as it rotates along the machine.

In general concept, in the first step of the present novel method, the plug member 10 is inserted into a means for receiving, orienting and retaining the plug members such as nest assembly 20. The nest assembly includes a pair of plug retaining members 22 and 24. Each plug retaining member can be formed of two halves which permit the plug retaining member to be opened in order to receive a given plug member and thereafter closed to contain the plug member therein. The combined plug retaining members further comprises an internal cylinder which contains a multiplicity of blow holes in its wall. Pressurized gas such as air under pressure is blown into the cylinder through the multiplicity of holes such that the air enters the foam or sponge-like plug member 10 through the multiplicity of open cells contained within such material. As a result, with its open cells being filled with air, the plug member becomes temporarily rigid and semi-hard. Thereafter, slits are made in one transverse wall of the plug member to accommodate one end of a flexible interconnecting member. Since the plug member is filled with air, it does not buckle under the impact of the knife members which are plunged into the plug member to create the slits. A predetermined length of flexible interconnecting member is then cut. A small amount of adhesive means is placed on each end of the flexible interconnecting member or alternatively at the location of the intersection of the slits in each plug member and thereafter one end of the interconnecting member is inserted into the slits formed in a first plug member and the second end of the interconnecting member is similarly inserted into the slits formed in a second plug member so as to create a pair of plug members interconnected by the flexible interconnecting member or cord. The adhesive serves as lubricant as well as a bonding agent to permit the cord to be inserted into the slits. This eliminates the necessity of having to create a wide opening in the plug member and inserting the cord and then waiting for the foam or other sponge like material of the plug member to return to its normal shape around the hole and close in around the inserted cord. As a result, the entire insertion process is far more efficient and the bond between the plug member and the interconnecting member is very strong.

Having thus described the concept of the present invention, a preferred embodiment of the present invention for performing this task will now be described. It will be appreciated that the apparatus as will now be described can be located on a mass production machine such as a rotary dial machine and the various steps can be performed at a multiplicity of different stations as the dial rotates and arrives at each given station assigned to perform a portion of the task. The invention will now be described with reference to FIGS. 2 through 13. As can be seen from the top plan view of FIGS. 2 and 3 and the side elevational view of FIG. 4, the nest assembly 20 of the present invention comprises a pair of plug retaining members 22 and 24. It is preferred that each plug retaining member include a chamber which is generally of the same shape as the plug member which it will receive. It is also preferred that the space of the internal chamber of each plug retaining member 22 and 24 be the same size as or slightly larger than the plug member so as to accommodate a volume of air. In one preferred embodiment as shown in FIG. 1, the plug member 10 is generally cylindrical in shape and therefore in one preferred embodiment of the present invention, each plug retaining member 22 and 24 includes a chamber which can be generally cylindrical in shape. As shown in FIGS. 3, 4, 5 and 6, plug retaining member 24 comprises a generally cylindrical chamber 72. Chamber 72 further comprises a multiplicity of tiny holes 26 which are located around the periphery of its longitudinal surface. The holes 26 extend through the entire thickness of the chamber wall and provide an air passageway into chamber 72 of plug retaining member 24.

Figure 5:
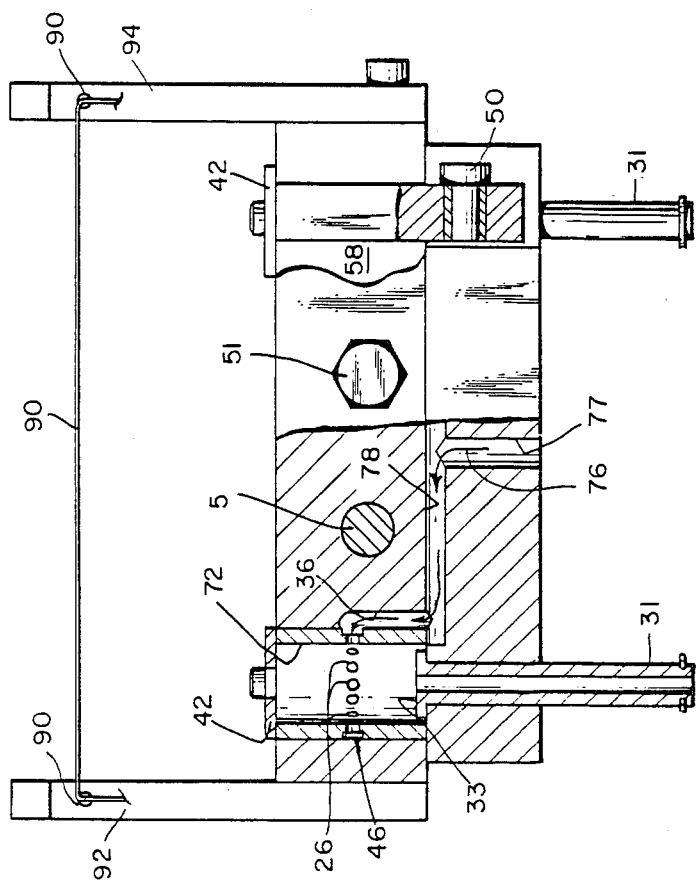
FIG. 5 is a rear elevational view in partial cross-section of the nest assembly.
Figure 10:
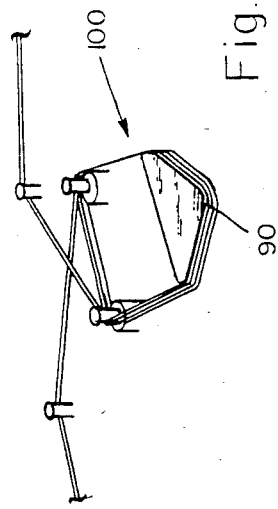
FIG. 10 is a perspective view of the winding assembly used to measure a predetermined amount of cord prior to inserting the ends of the cord into two plug members.

The plug receiving member 24 is formed of two halves, a stationary half 28 and a movable half 30. As shown in FIGS. 2, 3 and FIG. 5, first stationary half 28 is comprised of a one-half cylindrical wall 34 and includes a gap or an outer air chamber 36 between wall 34 and the body 35 of first stationary half 28 and one half of air-sleeve or collar 46 which is aligned with the holes 26. As shown in FIG. 4, first stationary half 28 also comprises a rotatable cover 32 connected to rotation means 38. Second movable half 30 comprises of a one-half cylindrical wall 44 and includes a gap or an outer air chamber 46 between wall 44 and the body 45 of movable half 30. Second movable half 30 also comprises a rotatable cover 42 connected to rotation means 50. As shown by the dotted lines in FIG. 4, covers 32 and 42 are cracked open or simultaneously rotated away from each other in order to form an opening 52 between covers 32 and 42. The angle of rotation for each cover can be from 10 to 15 degrees. In one preferred embodiment (as shown in FIGS. 2 and 3), a force exerted on cam 49 causes rods 54 and 56 and their respective associated spring means 53 and 55 to slide horizontally to the left. As best illustrated in FIG. 3, each rod 54 and 56 terminates in movable half 30 and therefore cause movable half 30 to slide horizontally away from fixed half 28 to create an oval shaped opening 52 in plug retaining member 24 and a comparable opening in plug retaining member 22. Each rod 54 and 56 also comprises a threaded bolt 51 and 57 respectively which protrudes out of the back end of body 45 of movable half 30. Referring to FIG. 4, as rod 54 is caused to slide horizontally, Bolt 51 is caused to abut upper inner wall 58 of cover 42, thereby causing it to rotate about rotation means 50 (such as a rod) in the counterclockwise direction. Simultaneously, a threaded bolt 59 which is attached to rod 54 by connecting member 61 is caused to slide horizontally and abut lower outer wall 39 of cover 32, thereby causing it to rotate in the clockwise direction by the same amount about rotation means 38. The angle of rotation of each cover can be from approximately ten (10) to fifteen (15) degrees. Therefore, the horizontal movement of movable half 30 and rotation of the covers creates an oval shaped opening 52 through which a plug member 10 can be inserted between halves 28 and 30.

When the force from cam 49 is released, return spring means 53 and 55 caused rods 54 and 56 to return to their original location. Bolts 51 and 53 caused movable half 30 to slide with rods 54 and 56 and return plug retaining members 22 and 24 to the closed position as shown in FIG. 2. In addition, bolt 51 slides away from inner wall 58 (as does bolt 53) and bolt 59 slides away from outer wall 39, thereby releasing the force against these walls. The two covers 32 and 42 are caused to rotate back to the their original position by return means 60 and 66. Return means 60 comprises a rod 62 and spring means 64 which cause cover 42 to rotate back to its original position. Return means 66 comprises a rod 68 and spring means 70 which cause cover 32 to rotate back to its original position. When stationary half 28 and movable half 30 are thus returned to their original positions, an internal plug retaining member chamber 72 is formed with the plug member 10 retained therein. As best illustrated in FIG. 5, the lower surface of chamber 72 is formed by the top 33 of plunger 31. Respective halves of air sleeve or collar 46 are joined to form one continuous air chamber surrounding the multiplicity of blow holes 26. As best shown in FIGS. 2 and 5, pressurized gas such as air 76 under pressure is then fed through line 77 into passageway 78 and then into gaps gap or chamber 36 and then into air-sleeve or collar 46 and from the collar 46 through holes 26 and into internal chamber 72. Since the plug member 10 is confined in chamber 72 between plunger top 33 at the bottom, covers 32 and 42 at the top and walls 34 and 44 on the sides, the plug member 10 is retained within the chamber 72 while gas 76 under pressure is forced into the chamber 72. As a result, as the gas 76 under pressure shoots through blow holes 26, it enters the foam or sponge-like plug member 10 through the multiplicity of open cells (best shown as 8 in FIGS. 7 and 8) contained within such material. As a result, with its open cells 8 being filled with gas 76, the plug member 10 becomes temporarily rigid and semi-hard. The process of inserting a sufficient amount of air into the plug member 10 may take only 1 to 5 seconds. Air can be supplied at 60 psi.

Figure 6:
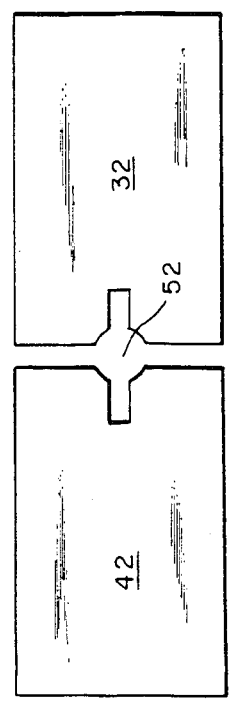
FIG. 6 is a top plan view of the two covers and associated opening therebetween of a plug retaining member.

In the next step of the method, a pair of hairline slits are made in the Top 6 of plug member 10 while it is being filled with gas 76. As can be seen in the illustration of retaining member 22 in FIG. 2 and also in FIG. 4 and the top plan view of FIG. 6, an opening 52 which includes slotted extensions as shown in FIG. 6 are formed by covers 32 and 42. The opening 52 is small enough to prevent the plug member 10 from coming out of chamber 72 and is large enough to permit knife members to enter the chamber 72 through opening 52 and penetrate Top 6 of plug member 10. The piercing members or knife blades 80 and 82 are shown in the schematic diagram of FIGS. 7 and 8. It will be appreciated that piercing member 80 is suspended from movable apparatus 84 which is suspended above the nest assembly 20 in the at rest position and is then lowered into operation at the desired time. Similarly, piercing member 82 is suspended from movable apparatus 86 which is suspended above the nest assembly 20 in the at rest position and is then lowered into operation at the desired time. Movable apparatus 84 and 86 are conventional mechanical assemblies which hold the piercing member at a given height until needed, serve to lower the piercing member in order to enable it to make a hairline slit in the plug member 10, and then return the piercing member to its elevated out of use position.

Figure 8:
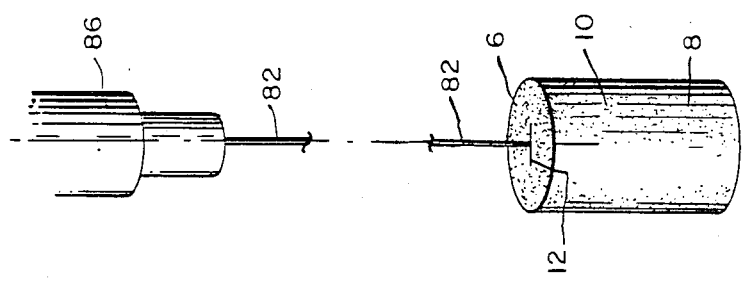
FIG. 8 is a perspective view a slit being cut in a plug by a second piercing member or knife in a direction approximately 90 degrees to the first slit, with the plug removed from the nest for illustrative purposes to show the plug in the semi-rigid position.
Figure 7:
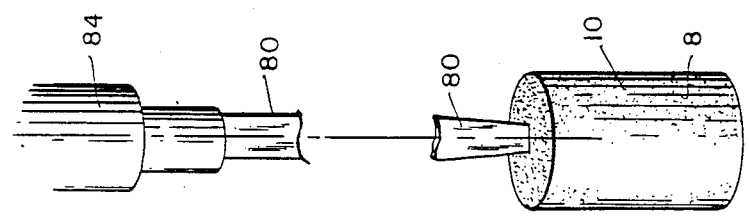
FIG. 7 is a perspective view a slit being cut in a plug by a first piercing member or knife, with the plug removed from the nest for illustrative purposes to show the plug in the semi-rigid position.

In operation, after the plug member 10 has been inserted into the chamber 72 as previously described, the nest assembly 20 is moved to another location around the rotary dial where knife 80 is suspended above cylinder 72 and plug member 10. While the plug member 10 is being filled with gas 76 in order to make it rigid, first piercing member or knife 80 is lowered so that the knife 80 is thrust into the plug member 10 and enters through opening 52 and penetrates the top 6 of plug member 10 to create a first hairline slit 12. first piercing member 80 is then returned to its at rest position. The nest assembly 20 is moved to another location around the rotary dial where knife 82 is suspended above cylinder 72 and plug member 10. While the plug member 10 is once again being filled with pressurized gas such as air 76 in order to make it rigid, second piercing member or knife 82 is lowered so that the knife 82 is thrust into the plug member 10 and enters through opening 52 and penetrates the top 6 of plug member 10 to create a second hairline slit 14. second piercing member 82 is then returned to its at rest position. The angle of the second knife 82 is approximately ninety (90) degrees to the first knife 80 so that a second transverse slit 14 is cut to the Top 6 of plug member 10. A perspective view of the cuts being made in the plug member and the resulting transverse slit is shown in FIGS. 7 through 9. Since the open cells 8 of plug member 10 are filled with gas 76 and it is semi-rigid, the plug member 10 does not buckle under the impact of the thrust from the knives 80 and 82 and permits a pair of slits 12 and 14 to be made in the top 6 of plug member 10. Assuming the plug member 10 is approximately one inch in vertical height, each slit 12 and 14 can be approximately one quarter of an inch deep. Of course, any other depth is also within the spirit and scope of the present invention. A very slow motion of the cutting blade or knife 80 and 82 toward the plug 10 will serve to deform rather than cut the plug. Therefore, in the preferred embodiment, the cutting speeds need to be fast enough so that the knife (80 and 82) will cut rather than deform the plug. By way of example, the preferred speed of the knives 80 and 82 as they move toward and into the plug should be greater than approximately six (6) inches per secondd. As an alternative to the use of gas, certain materials such as polyvinyl chloride will become semi-rigid when chilled. The chilled foam material can therefore be cut by the knife without deforming the plug.

The speed of the cutting means such as the knife can be an important factor in compensating for the non-rigidity of the foam. It has been discovered that if the cutting member is moving at a speed sufficiently high such as at least 75 inches per second for particular materials when penetrating the surface of the foam plug, this speed compensates for the non-rigidity and it is not necessary to fill the foam with gas in order to make it semi-rigid before the cut is made. Therefore, if the speed of the knife (80 and 82) is sufficiently high such as at least 75 inches per second, then the slit in the plug can be made without the necessity of blowing gas into the plug and therefore the plug can be made of foam material which is not necessarily open-celled foam. It will be appreciated that the remaining steps of the operation to be described are the same as for the open-celled material which is filled with gas prior to the insertion of the knife.

It will also be appreciated that a transverse slit can be made in one operation by thrusting a piercing member containing a crossed piercing edge into the top 6 of plug member 10. However, it has been discovered that such a piercing object does not create a smooth slit as is achieved by two separate piercing operations. The final result, regardless of method, is a hairline opening composed of transverse slits 12 and 14 in top 6 of plug assembly 10, as shown in FIG. 9.

In the next step of the operation, a given length of flexible interconnecting member or cord 90 is selected. The cord 90 is in tension stretched across posts 92 and 94 as shown in FIG. 5. As shown in the perspective view of FIG. 10, a winding assembly 100 of known circumference which is located intermediate adjacent next assemblies 20 causes a given length of interconnecting member 90 to be drawn from a spool and wrapped around the the circumference until the desired length is selected.

In the next step of the present invention, a liquid adhesive is applied. In one method as shown in FIG. 11, the liquid adhesive 102 is applied at the intersection of the hairline slits 12 and 14. In an alternative process, the liquid adhesive 102 is applied to the end of the cord (92 and 94) which will be placed into the slits 12 and 14. Either way, it has been discovered that with the hairline slits 12 and 14 made as described, the end 92 or 94 of the flexible interconnecting member 90 can actually be pushed into the slits 12 and 14 when liquid adhesive 102 is applied to either the slits or to the end of the flexible interconnecting member 90. This is because the liquid adhesive 102 will serve as a lubricant and permits the end 92 (or 94) of cord 90 to be inserted into the intersection of the hairline slits 12 and 14. This eliminates the necessity of having to create a wide opening in the plug member 10 and inserting the cord and then waiting for the foam or other sponge like material of the plug member to return to its normal shape around the hole and close in around the inserted cord. As a result, the entire insertion process is far more efficient and the bond between the plug member 10 and the flexible interconnecting member 90 is far stronger. A perspective view of an end 92 being inserted into slits 12 and 14 with liquid adhesive 102 used on the slits is shown in FIG. 12. A conventional arm member or robot means 104 is used to take the cut end from post 92 (or 94) and insert it into the plug member 10. In actual operation, the nest assembly 20 is rotated to one station where the liquid adhesive is applied to the slits and then the nest assembly is rotated to another station on the rotary dial where the flexible interconnecting member 90 is cut to the desired length by conventional razor blade cutting apparatus which can be manipulated from a robot arm and then the end (92 or 94) of cord 90 is inserted into the plug member 90.

The entire process has been described with a single plug member. It will be appreciated that the entire method described can be performed simultaneously on two separate plug members 10, one in first plug retaining member 22 and simultaneously in second plug retaining member 24. Each step of insertion of the plug member in the plug retaining member, the adding of air under pressure while slits are being cut, the cutting of the slits and the application of the adhesive can be performed simultaneously on both plug members. The cord 90 can be cut intermediate the two plug members so that one end 92 is inserted into one plug member and the other end 94 is inserted into the other plug member.

Alternatively, as shown in FIG. 13, the flexible interconnecting member 90 can be positioned so that one end is inserted into one plug member in one nest assembly 20 and the other end of the flexible interconnecting member can be inserted into a plug member in an adjacent nest assembly 20. The completed ear plug assembly 120 is shown in FIG. 14. The flexible interconnecting member or cord 90 is shown broken for purposes of illustrating the relative length of the flexible interconnecting member 90 relative to the short length of the plug members 10.

After the cord 90 has been inserted into the pair of plug members 10, the plug retaining members are once again opened by relative rotation of covers (such as 32 and 42) and lateral sliding movement of movable half (such as 30) as previously described to permit opening 52 to be wide enough to allow the plug member 10 to be removed. The plunger 31 is then caused to move upwardly so that its top 33 enters into the cylinder 72 and ejects the plug member 10 from the plug retaining member.

A schematic top plan view of the rotary dial 125 showing the apparatus as previously described in relative positions is shown in FIG. 13. At Station 1, the nest assembly is at its starting state. At Station 2, the plug retaining members 22 and 24 are opened to each receive a plug 10 as previously described from a plug reservoir 19. The plug retaining members 22 and 24 are then closed and the nest assembly moved to Station 3. At Station 3, the plugs 10 are filled with air as previously described and knife members 80 cut a slit 12 in one direction in the top of each Plug. The nest assembly then moves to Station 4 where a knife cuts a slit 14 at approximately ninety degrees to slit 12 in the top of each plug 10 while the plug is once again filled with air. At station 5, adhesive is applied at the intersection of the slits in the top of the plug 10. At station 6, a given length of cord 90 is selected by the winding apparatus 100 and the ends are cut by robot arm 104, and then the ends of the cords are inserted into the slits by conventional apparatus which takes a hold of each end 92 and 94 and thrusts the cord 90 into a respective pair of slits. At Station 7, the completed ear plug assembly 120 is ejected into a container 130. The nest assembly then returns to Station 1 where the process is begun over again. The process is a continuous process with each station being active in its assigned task as the multiplicity of nest assemblies rotates around the dial from station to station.

Through use of the method and apparatus as described, the ear plug assembly can be made in a very rapid and efficient manner without the necessity of requiring a substantial crevice to be inserted into the Plug Member. In addition, the semi-rigid state created in the foam or sponge-like plug member assures a clean sharp cut without distortion of the entire Plug Member when the piercing members are trust into the plug member.

Of course the present invention is not intended to be restricted to any particular method or form or arrangement, or any specific embodiment disclosed herein, or any specific use, since the same may be modified in various particulars or relations without departing from the spirit or scope of the claimed invention hereinabove shown and described of which the apparatus shown is intended only for illustration and for disclosure of an operative embodiment and not to show all of the various forms or modification in which the invention might be embodied or operated.

The invention has been described in considerable detail in order to comply with the patent laws by providing full public disclosure of at least one of its forms. However, such detailed description is not intended in any way to limit the broad features or principles of the invention, or the scope of patent monopoly to be granted.

What is claimed is:

1. The method of inserting an end of a flexible interconnecting means, used to connect a pair of plug members composed of at least partially open cell foam material and which serve as ear plugs, into a respective plug member, comprising:
   a. placing the plug member into an enclosed chamber which contains a multiplicity of blow holes in its surface and an opening in one transverse surface;
   b. forcing pressurized gas through said blow holes which gas in turn flows into the open cells of the at least partially open cell foam material from which each plug member is made;
   c. inserting a first piercing member through said opening in the lateral surface of said chamber and into one lateral surface of said plug member while it is being filled with pressurized gas and thereafter removing the piercing member to thereby create a first hairline slit within the lateral surface of said plug member;
   d. inserting a second piercing member in a direction generally perpendicular to the direction of said first piercing member through said opening in the lateral surface of of said chamber and into the lateral surface of said plug member while it is being filled with pressurized gas and thereafter removing the second piercing member to thereby create a second hairline slit approximately perpendicular to and crossing the approximate centerline of said first hairline slit within the lateral surface of said plug member;
   e. placing adhesive adjacent to the intersection of said first and second hairline slits;
   f. selecting a given length of interconnecting member and cutting the interconnecting member to form two ends;
   g. inserting one end of said interconnecting member into said plug member at the location of the intersection of said first and second hairline slits; and
   h. removing said plug member from said chamber.

2. The invention as defined in claim 1 wherein said at least partially open cell foam material is polyurethane.

3. The invention as defined in claim 1 wherein said at least partially open cell foam material is polyvinyl chloride.

4. The invention as defined in claim 1 wherein said flexible interconnecting means is a cord.

5. The invention as defined in claim 1 wherein the speed of said first piercing member is greater than six inches per second when inserted into the plug member and the speed of said second piercing member is greater than six inches per second when inserted into the plug member.

6. The method of inserting a cord into a surface of a plug member composed of at least partially open cell foam material comprising:
   a. filling the at least partially open cell foam material with gas;
   b. cutting at least one slit in a surface of said plug member while it is being filled with gas;
   c. applying adhesive at the location of said at least one slit; and
   d. selecting a given length of cord and cutting the cord to form two ends;
   e. inserting one end of said cord into said at least one slit at the location of said adhesive.

7. The method of inserting a cord into a surface of a plug member composed of at least partially open cell foam material comprising:
   a. filling the at least partially open cell foam material with gas;
   b. cutting at least one slit in a surface of said plug member while it is being filled with gas;
   c. selecting a given length of cord and cutting the cord to form two ends;
   d. applying adhesive at the location of one end of said cord; and
   e. inserting the end of said cord to which adhesive has been applied into said at least one slit.

8. The method of inserting an end of a flexible interconnecting means, used to connect a pair of plug members composed of at least partially open cell foam material and which serve as ear plugs, into a respective plug member, comprising:
   a. placing the plug member into an enclosed chamber which contains a multiplicity of blow holes in its surface and an opening in one transverse surface;
   b. forcing pressurized gas through said blow holes which gas in turn flows into the open cells of the at least partially open cell foam material from which each plug member is made;
   c. inserting a first piercing member through said opening in the lateral surface of said chamber and into one lateral surface of said plug member while it is being filled with pressurized gas and thereafter removing the piercing member to thereby create a first hairline slit within the lateral surface of said plug member;
   d. inserting a second piercing member in a direction at an angle to the direction of said first piercing member through said opening in the lateral surface of said chamber and into the lateral surface of said plug member while it is being filled with pressurized gas and thereafter removing the second piercing member to thereby create a second hairline slit which intersects said first hairline slit within the lateral surface of said plug member;
   e. placing adhesive adjacent to the intersection of said first and second hairline slits;
   f. selecting a given length of interconnecting member and cutting the interconnecting member to form two ends;
   g. inserting one end of said interconnecting member into said plug member at the location of the intersection of said first and second hairline slits; and
   h. removing said plug member from said chamber.

9. The invention as defined in claim 8 wherein said at least partially open cell foam material is polyurethane.

10. The invention as defined in claim 8 wherein said at least partially open cell foam material is polyvinyl chloride.

11. The invention as defined in claim 8 wherein said flexible interconnecting means is a cord.

12. The invention as defined in claim 8 wherein the speed of said first piercing member is greater than six inches per second when inserted into the plug member and the speed of said second piercing member is greater than six inches per second when inserted into the plug member.

13. The method of inserting an end of a flexible interconnecting means, used to connect a pair of plug members composed of at least partially open cell foam material and which serve as ear plugs, into a respective plug member, comprising:
 a. placing the plug member into an enclosed chamber which contains a multiplicity of blow holes in its surface and an opening in one transverse surface;
 b. forcing pressurized gas through said blow holes which gas in turn flows into the open cells of the at least partially open cell foam material from which each plug member is made;
 c. inserting a first piercing member through said opening in the lateral surface of said chamber and into one lateral surface of said plug member while it is being filled with pressurized gas and thereafter removing the piercing member to thereby create a first hairline slit within the lateral surface of said plug member;
 d. inserting a second piercing member in a direction at an angle to the direction of said first piercing member through said opening in the lateral surface of said chamber and into the lateral surface of said plug member while it is being filled with pressurized gas and thereafter removing the second piercing member to thereby create a second hairline slit which intersects said first hairline slit within the lateral surface of said plug member;
 e. selecting a given length of interconnecting member and cutting the interconnecting member to form two ends;
 f. placing adhesive adjacent the ends of said interconnecting member;
 g. inserting one end of said interconnecting member into said plug member at the location of the intersection of said first and second hairline slits; and
 h. removing said plug member from said chamber.

14. The method of inserting an end of a flexible interconnecting means, used to connect a pair of plug members composed of at least partially open cell foam material and which serve as ear plugs, into a respective plug member, comprising:
 a. placing the plug member into an enclosed chamber which contains a multiplicity of blow holes in its surface and an opening in one transverse surface;
 b. forcing pressurized gas through said blow holes which gas in turn flows into the open cells of the at least partially open cell foam material from which each plug member is made;
 c. inserting a criss-crossed piercing member through said opening in the lateral surface of said chamber and into one lateral surface of said plug member while it is being filled with pressurized gas and thereafter removing the piercing member to thereby create a pair of crossed hairline slits within the lateral surface of said plug member;
 d. placing adhesive adjacent to the intersection of said first and second hairline slits;
 e. selecting a given length of interconnecting member and cutting the interconnecting member to form two ends;
 f. inserting one end of said interconnecting member into said plug member at the location of the intersection of said first and second hairline slits; and
 g. removing said plug member from said chamber.

15. The method of inserting an end of a flexible interconnecting means, used to connect a pair of plug members composed of foam material and which serve as ear plugs, into a respective plug member, comprising:
 a. placing the plug member into an enclosed chamber which contains an opening in one transverse surface;
 b. inserting a first piercing member through said opening in the lateral surface of said chamber and into one lateral surface of said plug member at a speed of at least 75 inches per second to thereby create a first hairline slit within the lateral surface of said plug member and thereafter removing the piercing member;
 c. inserting a second piercing member in a direction generally perpendicular to the direction of said first piercing member through said opening in the lateral surface of said chamber and into the lateral surface of said plug member at a speed of at least 75 inches per second to thereby create a second hairline slit approximately perpendicular to and crossing the approximate centerline of said first hairline slit within the lateral surface of said plug member and thereafter removing the second piercing member;
 d. placing adhesive adjacent to the intersection of said first and second hairline slits;
 e. selecting a given length of interconnecting member and cutting the interconnecting member to form two ends;
 f. inserting one end of said interconnecting member into said plug member at the location of the intersection of said first and second hairline slits; and
 g. removing said plug member from said chamber.

16. The method of inserting a cord into a surface of a plug member composed of foam material comprising:
 a. cutting at least one slit in a surface of said plug member while the cutting instrument is moving at a speed of at least 75 inches per second;
 b. applying adhesive at the location of said at least one slit;
 c. selecting a given length of cord and cutting the cord to form two ends; and
 d. inserting one end of said cord into said at least one slit at the location of said adhesive.

17. The method of inserting a cord into a surface of a plug member composed of foam material comprising:
 a. cutting at least one slit in a surface of said plug member while the cutting instrument is moving at a speed of at least 75 inches per second;
 b. selecting a given length of cord and cutting the cord to form two ends;
 c. applying adhesive at the location of one end of said cord; and
 d. inserting the end of said cord to which adhesive has been applied into said at least one slit at the location of said adhesive.

18. The method of inserting an end of a flexible interconnecting means, used to connect a pair of plug members composed of foam material and which serve as ear plugs, into a respective plug member, comprising:
 a. placing the plug member into an enclosed chamber which contains an opening in one transverse surface;
 b. inserting a first piercing member through said opening in the lateral surface of said chamber and into one lateral surface of said plug member at a speed of at least 75 inches per second and thereafter removing the piercing member to thereby create a first hairline slit within the lateral surface of said plug member;

c. inserting a second piercing member in a direction at an angle to the direction of said first piercing member through said opening in the lateral surface of said chamber and into the lateral surface of said plug member at a speed of at least 75 inches per second and thereafter removing the second piercing member to thereby create a second hairline slit which intersects said first hairline slit within the lateral surface of said plug member;

d. placing adhesive adjacent to the intersection of said first and second hairline slits;

e. selecting a given length of interconnecting member and cutting the interconnecting member to form two ends;

f. inserting one end of said interconnecting member into said plug member at the location of the intersection of said first and second hairline slits; and g. removing said plug member from said chamber.

19. The method of inserting an end of a flexible interconnecting means, used to connect a pair of plug members composed of foam material and which serve as ear plugs, into a respective plug member, comprising:

a. placing the plug member into an enclosed chamber which contains an opening in one transverse surface;

b. inserting a first piercing member through said opening in the lateral surface of said chamber and into one lateral surface of said plug member at a speed of at least 75 inches per second and thereafter removing the piercing member to thereby create a first hairline slit within the lateral surface of said plug member;

c. inserting a second piercing member in a direction at an angle to the direction of said first piercing member through said opening in the lateral surface of said chamber and into the lateral surface of said plug member at a speed of at least 75 inches per second and thereafter removing the second piercing member to thereby create a second hairline slit which intersects said first hairline slit within the lateral surface of said plug member;

d. selecting a given length of interconnecting member and cutting the interconnecting member to form two ends;

e. placing adhesive adjacent the ends of said interconnecting member;

f. inserting one end of said interconnecting member into said plug member at the location of the intersection of said first and second hairline slits; and g. removing said plug member from said chamber.

20. The method of inserting an end of a flexible interconnecting means, used to connect a pair of plug members composed of foam material and which serve as ear plugs, into a respective plug member, comprising:

a. placing the plug member into an enclosed chamber which contains an opening in one transverse surface;

b. inserting a criss-crossed piercing member through said opening in the lateral surface of said chamber and into one lateral surface of said plug member at a speed of at least 75 inches per second and thereafter removing the piercing member to thereby create a pair of crossed hairline slits within the lateral surface of said plug member;

c. placing adhesive adjacent to the intersection of said first and second hairline slits;

d. selecting a given length of interconnecting member and cutting the interconnecting member to form two ends;

e. inserting one end of said interconnecting member into said plug member at the location of the intersection of said first and second hairline slits; and f. removing said plug member from said chamber.

21. The method of inserting a cord into a surface of a plug member composed of at least partially open cell foam material comprising:

a. chilling said plug member so that it is semi-rigid;

b. cutting at least one slit in a surface of said plug member while it is semi-rigid;

c. applying adhesive at the location of said at least one slit; and d. selecting a given length of cord and cutting the cord to form two ends;

e. inserting one end of said cord into said at least one slit at the location of said adhesive.

22. The method of inserting a cord into a surface of a plug member composed of at least partially open cell foam material comprising:

a. chilling said plug member so that it is semi-rigid;

b. cutting at least one slit in a surface of said plug member while it is being filled with gas;

c. selecting a given length of cord and cutting the cord to form two ends;

d. applying adhesive at the location of one end of said cord; and e. inserting the end of said cord to which adhesive has been applied into said at least one slit.

* * * * *